United States Patent [19]

Klein et al.

[11] Patent Number: 5,599,848
[45] Date of Patent: Feb. 4, 1997

[54] PREPARATION, INTERMEDIATES FOR THE PREPARATION AND THE USE OF A MIXTURE OF DODECDIENOL ISOMERS

[75] Inventors: Ulrich Klein, Limburgerhof; Ulrich Neumann, Schifferstadt; Wolfgang Mackenroth, Bad Duerkheim; Guenter Renz, Mannheim; Wolfgang Krieg, Weingarten; Christiane Mackenroth, Bad Duerkheim; Ernst Buschmann, Ludwigshafen; Jacobus J. DeKramer, Limburgerhof; Roland Milli, Ilvesheim, all of Germany

[73] Assignee: BASF Aktiengesellschaft, Ludwigshafen, Germany

[21] Appl. No.: 512,259

[22] Filed: Aug. 7, 1995

Related U.S. Application Data

[63] Continuation of Ser. No. 211,451, Mar. 31, 1994, abandoned.

[30] Foreign Application Priority Data

Oct. 24, 1991 [DE] Germany .......................... 41 35 064.2

[51] Int. Cl.$^6$ .................................................. A01N 31/02
[52] U.S. Cl. .......................... 514/739; 568/591; 568/596; 568/598; 568/903
[58] Field of Search ............................................. 514/739

[56] References Cited

U.S. PATENT DOCUMENTS

| | | | |
|---|---|---|---|
| 3,852,419 | 12/1974 | Roelofs et al. | 514/739 |
| 3,985,813 | 10/1976 | Labovitz et al. | 568/596 |
| 4,189,614 | 2/1980 | Samain et al. | |
| 4,973,765 | 11/1990 | MacKenroth et al. | 568/903 |

FOREIGN PATENT DOCUMENTS

| | | |
|---|---|---|
| 4101878 | 7/1992 | Germany . |
| 1299691 | 12/1972 | United Kingdom . |

OTHER PUBLICATIONS

Ent. exp. & appl. 16, 341 (1973), Minks et al.
Synthesis (5) 359 (1981) Rossi et al.
Am. Chem. Soc., 100,4878 (1979) Chapman et al.
Bull. Soc. Chim. Fr. [3]31, 1204, Bouveault et al.
Chem. Ind., (1964), 171, Chladek et al.
Liebigs Ann. Chem., 601, 84 (1956).
J. Org. Chem., 7, 326 (1942), Henze et al.
Bull. Soc. Chim. Belg., 22, 410 (1908) Chavamie et al.
Tetrahedron Lett., 18, 1465 (1975) Normant et al.
CA Service, Registry Hand book, RN 85576-23-4 (1983).
CA Service, Registry Handbook, RN 11752-77-9 (1988).

*Primary Examiner*—Joseph E. Evans
*Attorney, Agent, or Firm*—Keil & Weinkauf

[57] ABSTRACT

A process for preparing a mixture of 8E,10E-dodecadienol (Ia), 8E,10Z-dodecadienol (Ib), 8Z,10E-dodecadienol (Ic) and 8Z,10Z-dodecadienol (Id), $$H_3C-CH=CH-CH=CH-(CH_2)_6-CH_2-OH$$

(8E,10E=Ia)
(8E,10Z=Ib)
(8Z,10E=Ic)
(8Z,10Z=Id)

starting from 1,8-octanediol (II) which is converted with a halogenating agent into (III)

$$Hal-CH_2-(CH_2)_6-CH_2-OH \quad (III)$$

where (III) is subsequently reacted with (IV), $$H_2C=CH-O-R \quad (IV)$$

to give (V)

$$Hal-CH_2-(CH_2)_6-CH_2-O-CH(CH_3)-OR \quad (V),$$

(V) is converted in the presence of magnesium and crotonaldehyde into (VI)

$$H_3C-CH=CH-CH(OH)-(CH_2)_8-O-CH(CH_3)-OR \quad (VI)$$

and the protective group R and the hydroxyl group are simultaneously eliminated from (VI) in the presence of acid, novel intermediates for this process, and methods for controlling the codling moth *Cydia pomonella* by interfering with mating using this mixture are described.

3 Claims, No Drawings

PREPARATION, INTERMEDIATES FOR THE PREPARATION AND THE USE OF A MIXTURE OF DODECDIENOL ISOMERS

This application is a continuation of application Ser. No. 08/211,451, filed on Mar. 31, 1994, now abandoned.

The present invention relates to a process for preparing a mixture of 8E,10E-dodecadienol (Ia), 8E,10Z-dodecadienol (Ib), 8Z,10E-dodecadienol (Ic) and 8Z,10Z-dodecadienol (Id),

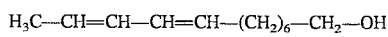

(8E,10E=Ia)
(8E,10Z=Ib)
(8Z,10E=Ic)
(8Z,10Z=Id)

which comprises converting 1,8-octanediol (II)

$$HO-CH_2-(CH_2)_6-CH_2-OH \quad (II)$$

in a conventional manner in a solvent in the presence of a halogenating agent into a halo derivative of the formula (III)

$$Hal-CH_2-(CH_2)_6-CH_2-OH \quad (III)$$

where Hal is halogen, subsequently reacting (III) with a vinyl ether of the formula (IV), $$H_2C=CH-O-R \quad (IV)$$

where R is a C-organic radical, in a conventional manner in the presence of an acid to give an acetal of the formula (V)

$$Hal-CH_2-(CH_2)_6-CH_2-O-CH(CH_3)-OR \quad (V),$$

converting (V) in the presence of magnesium and crotonaldehyde into an alkenol of the formula (VI)

$$H_3C-CH=CH-CH(OH)-(CH_2)_8-O-CH(CH_3)-OR \quad (VI)$$

and simultaneously eliminating from (VI) in the presence of acid the protective group R and the hydroxyl group.

The present invention also relates to novel intermediates for this process and to methods for controlling the codling moth *Cydia pomonella* by using this mixture to interfere with mating.

The codling moth is an important pest of apple crops.

To date the codling moth has been controlled non-specifically by conventional methods, ie. by application of insecticides. It has been possible to apply a specific method after identification of the sex attractant of the codling moth (Roeloffs et al. DE-A 21 23 434). It is known that in butterflies females which are ready to mate produce sex attractants (pheromones) and secrete them into the environment. Male butterflies of the same species are then able to find the females with the aid of this odoriferous substance.

There are in principle three possible ways of applying sex attractants to crop protection:

1. Monitoring technique

Pheromone traps containing synthetic sex attractant baits are suspended in areas of potential infestation. The presence of male lepidoptera in the trap demonstrates that the pest has appeared. It is additionally possible to derive information about the level of infestation and the correct timing of control measures.

2. Trapping technique

It is possible to combine the attractant with insecticidal agents. Insecticides can be added to the bait or the trap or else used to treat only the immediate vicinity of the trap so that most of the male lepidoptera attracted from a distance can be killed. The population in the biotope is reduced to an acceptable level.

3. Interference with mating method

Finally, the pest can be controlled by saturating the air with sex attractants or substances with a similar action, which interferes with the finding of the females by the male butterflies. This prevents the insects mating.

In the latter case a large amount of the attractant is distributed in the air throughout the crop to be protected so that the males are able to detect the scent everywhere, which interferes with their normal direction finding.

The third method (interference with mating) in particular is an extremely selective and effective way of controlling an unwanted species while leaving non-target organisms, especially all beneficial species, unaffected.

In addition, this method requires only relatively small amounts of the agents, often corresponding only to fractions of the conventional doses of classical insecticidal agents (cf. Birch ed., Pheromones, North Holland Publ. Co., 1974).

The disadvantage of methods 1 and 2 is that the attractant of synthetic origin must be exactly identical in structure and purity to its natural counterpart (Minks and Voermann, Entomologia exp. and appl. 16 (1973) 341–49 and Wegler, Chemie der Pflanzenschutz- und Schädlings-bekämpfungsmittel (1981) vol. 6, page 167). Technical mixtures or the like have regularly failed in trapping tests.

It was to be assumed on the basis of the experience gained with methods 1 and 2 that method 3 would also be effective only with highly pure pheromone of the codling moth. This is why to date only pure 8E,10E-dodecadienol has been employed for the mating interference method (G. H. L. Rothschild, Insect. Suppr. Controlled Release Pheromonic Syst. Vol. 2, 117–34).

We have now found that, surprisingly, a mixture of the 4 stereoisomers 8E,10E-dodecadienol (Ia), 8E,10Z-dodecadienol (Ib), 8Z,10E-dodecadienol (Ic) and 8Z,10Z-dodecadienol (Id) can likewise be employed successfully for interfering with mating.

The mixture is obtained particularly advantageously by converting 1,8-octanediol (II) in a conventional manner in a solvent in the presence of a halogenating agent into a halo derivative of the formula (III), subsequently reacting (III) with a vinyl ether of the formula (IV) in the presence of an acid to give the acetal of the formula (V), converting (V) in the presence of magnesium and crotonaldehyde into an alkenol of the formula (VI) and simultaneously eliminating the protective group and the hydroxyl group from (VI) in the presence of acid.

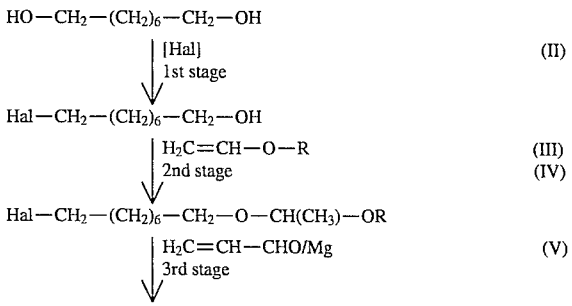

-continued

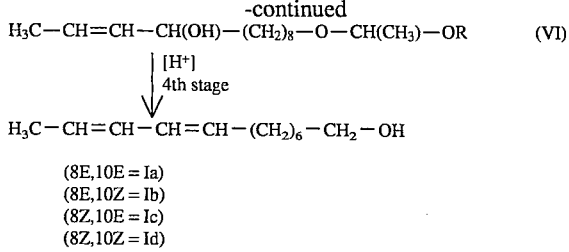

(8E,10E = Ia)
(8E,10Z = Ib)
(8Z,10E = Ic)
(8Z,10Z = Id)

Hal in formulae (III) and (V) is halogen such as fluorine, chlorine, bromine and iodine, preferably chlorine and bromine.

R in formulae (IV), (V) and (VI) is a C-organic radical, preferably alkyl of up to eight carbons such as, in particular, methyl, ethyl, propyl, 1-methylethyl, butyl, 1-methylpropyl, 2-methylpropyl and 1,1-dimethylpropyl, cycloalkyl of up to six carbons such as, in particular, cyclopropyl, cyclobutyl, cyclopentyl and cyclohexyl, and haloalkyl of up to eight carbons such as, in particular, straight-chain alkyl which is substituted once or twice in the terminal position by fluorine, chlorine or bromine, such as 2-fluoroethyl, 3-fluoropropyl, 4-fluorobutyl, 5-fluoropentyl, 6-fluorohexyl, 7-fluoroheptyl, 8-fluorooctyl, 2-chloroethyl, 3-chloropropyl, 4-chlorobutyl, 5-chloropentyl, 6-chlorohexyl, 7-chloroheptyl, 8-chlorooctyl, 2-bromoethyl, 3-bromopropyl, 4-bromobutyl, 5-bromopentyl, 6-bromohexyl, 7-bromoheptyl, 8-bromooctyl, 2,2-difluoroethyl, 3,3-difluoropropyl, 4,4-difluorobutyl, 5,5-difluoropentyl, 6,6-difluorohexyl, 7,7-difluoroheptyl, 8,8-difluorooctyl, 2,2-dichloroethyl, 3,3-dichloropropyl, 4,4-dichlorobutyl, 5,5-dichloropentyl, 6,6-dichlorohexyl, 7,7-dichloroheptyl, 8,8-dichlorooctyl, 2,2-dibromoethyl, 3,3-dibromopropyl, 4,4-dibromobutyl, 5,5-dibromopentyl, 6,6-dibromohexyl, 7,7-dibromoheptyl, and 8,8-dibromooctyl.

The individual stages in this preparation process are carried out as follows:

1st stage (Rossi, Synthesis (1981) 359; Chapman et al., J. Am. Chem. Soc., 100 (1979) 4878)

This reaction of (II) with a halogenating agent is normally carried out at from 20° to 180° C., preferably 80° to 120° C.

Suitable solvents are aliphatic hydrocarbons such as pentane, hexane, cyclohexane and petroleum ether, aromatic hydrocarbons such as toluene, o-, m- and p-xylene, halohydrocarbons such as methylene chloride, chloroform and chlorobenzene, ethers such as diethyl ether, diisopropyl ether, tert-butyl methyl ether, dioxane, anisole and tetrahydrofuran. Nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide and dimethylformamide, particularly preferably toluene, o-, m- and p-xylene and chlorobenzene.

It is also possible to use mixtures of the said solvents.

Suitable halogenating agents are phosphorus tribromide, phosphorus trichloride and thionyl chloride, preferably hydrogen bromide and hydrogen iodide, in particular hydrogen chloride.

The halogenating agents are generally employed in equimolar amounts but they can also be used in excess or, where appropriate, as solvent.

The precursors are generally reacted together in equimolar amounts. When hydrogen halides are used it may be advantageous for the yield to employ the acids in more or less than the stoichiometric ratio to octanediols.

1,8-octanediol, which is required to prepare the derivatives (III), is disclosed in the literature (Bouveault et al., Bull. Soc. Chim. Fr. [3] 31, 1204).

The reaction mixtures are worked up in a conventional manner, e.g. by mixing with water, separating the phases and, if necessary, purifying the crude products by chromatography. The intermediates and final products are in some cases colorless or pale brown viscous oils which can be purified or freed of volatiles under reduced pressure and at moderately elevated temperature. Where the intermediates and final products are obtained as solids, they can also be purified by recrystallization or digestion.

2nd stage (Chládek et al., Chem. Ind. (1964) 171)

This reaction of (III) with (IV) is normally carried out at from −20° to 60° C., preferably 0° to 20° C.

Suitable solvents are aliphatic hydrocarbons such as pentane, hexane, cyclohexane and petroleum ether, aromatic hydrocarbons such as toluene, o-, m- and p-xylene, halohydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide and dimethylformamide, particularly preferably ethers such as tetrahydrofuran and tert-butyl methyl ether.

It is also possible to use mixtures of the said solvents. The reaction can also be carried out without solvent.

The acids and acidic catalysts used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, benzenesulfonic acid, o-, m- and p-toluene-sulfonic acid, oxalic acid, citric acid and trifluoroacetic acid.

The acids are generally employed in catalytic amounts but they can also be used in equimolar amounts, in excess or, where appropriate, as solvent.

The precursors are generally reacted together in equimolar amounts. It may be advantageous for the yield to employ the vinyl ether in more or less than the stoichiometric ratio to chlorooctanol.

The vinyl ethers of the formula (IV) required for preparing the derivatives (V) are disclosed in the literature (Reppe, Liebigs Ann. Chem. 601 (1956) 84) or they can be prepared by the methods described therein.

The reaction mixtures are worked up in a conventional manner, e.g. by mixing with water, separating the phases and, if necessary, purifying the crude products by chromatography. The intermediates and final products are in some cases colorless or pale brown viscous oils which can be purified or freed of volatiles under reduced pressure and at moderately elevated temperature. Where the intermediates and final products are obtained as solids, they can also be purified by recrystallization or digestion.

3rd Stage (Henze et al., J. Org. Chem. 7 (1942) 326)

This reaction of (V) with crotonaldehyde in the presence of magnesium is normally carried out at from −20° to 80° C., preferably 0° to 40° C.

Suitable solvents are aliphatic hydrocarbons such as pentane, hexane, cyclohexane and petroleum ether, aromatic hydrocarbons such as toluene, o-, m- and p-xylene, halohydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and dimethyl sulfoxide and dimethylformamide, particularly preferably ethers such as diethyl ether and tetrahydrofuran.

It is also possible to use mixtures of the said solvents.

Magnesium is generally employed in the form of turnings in equimolar amounts but it can also be used in an excess of 0.1–100 mol %, preferably 0.1–50 mol %, in particular 0.1–20 mol %.

The precursors (V and crotonaldehyde) are generally reacted together in equimolar amounts. It may be advantageous for the yield to employ crotonaldehyde in an excess of 0.1–50 mol %, preferably 0.1–20 mol %, in particular 0.1–10 mol %, based on (V).

The reaction mixtures are worked up in a conventional manner, e.g. by mixing with water, separating the phases and, if necessary, purifying the crude products by chromatography. The intermediates and final products are in some cases colorless or pale brown viscous oils which can be purified or freed of volatiles under reduced pressure and at moderately elevated temperature. Where the intermediates and final products are obtained as solids, they can also be purified by recrystallization or digestion.

4th Stage
(Chavarnie et al., Bull. Soc. Chim. Belg. 22 (1908) 410)

The elimination of the protective group and simultaneously of the hydroxyl group is normally carried out at from −20° to 150° C., preferably 40° to 80° C.

Suitable solvents are aliphatic hydrocarbons such as pentane, hexane, cyclohexane and petroleum ether, aromatic hydrocarbons such as toluene, o-, m- and p-xylene, and high-boiling compounds such as di-$C_1$–$C_8$-alkyl phthalates such as dimethyl phthalate, diethyl phthalate, dipropyl phthalate, di-1-methylethyl phthalate, dibutyl phthalate, dipentyl phthalate, dihexyl phthalate, dioctyl phthalate and di-2-ethylhexyl phthalate, particularly preferably dibutyl phthalate, dipentyl phthalate, dihexyl phthalate and di-2-ethylhexyl phthalate.

It is also possible to use mixtures of the said solvents.

The acids and acidic catalysts used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid.

The acids are generally employed in catalytic amounts but they can also be used in equimolar amounts, in excess or, where appropriate, as solvent.

It has proven particularly advantageous for the synthesis of the dodecadienols (Ia) to (Id) from VI to react VI with acetic anhydride and sulfuric acid [Chavarnie, van Roelen, Bull. Soc. Chim. Belg. 22 (1908) 410] in cyclic and acyclic ethers such as diethyl ether, tetrahydrofuran or dioxane, aromatic hydrocarbons such as benzene, toluene or xylene, aliphatic hydrocarbons such as pentane, hexane, heptane or cyclohexane, or halohydrocarbons such as dichloromethane, dichloroethane or trichloroethane at from −20° to 100° C.

This entails in one reaction step both water and the protective group being eliminated.

The mixture obtained in this way can be subjected to an isomerization in order to increase the content of 8E,10E-dodecadienol.

This entails heating with catalytic amounts of 4-chlorothiophenol, 3-chtorothiophenol, thiophenol or mercaptoacetic acid and subsequently extracting the catalyst by washing with sodium hydroxide solution.

The isomerization can also be carried out by UV radiation in the presence of iodine or diphenyl disulfide.

The reaction mixtures are worked up in a conventional manner, eg. by mixing with water, separating the phases and, if necessary, purifying the crude products by chromatography. The intermediates and final products are in some cases colorless or pale brown viscous oils which can be purified or freed of volatiles under reduced pressure and at moderately elevated temperature. Where the intermediates and final products are obtained as solids, they can also be purified by recrystallization or digestion.

The mixture of compounds (Ia), (Ib), (Ic) and (Id) obtained by this process is suitable for controlling the codling moth *Cydia pomonella* by interfering with mating.

The mixture can be applied together with conventional aids, e.g. appropriately prepared plastic strips, twine, attractant-filled ampoules or the like (for example as described in DE-A 41 01 878) and can also contain impurities derived from the preparation.

The mixture can be formulated in both liquid and solid preparations. Suitable solvents are high-boiling, aromatic, aliphatic or cycloaliphatic compounds. Besides hydrocarbons, particularly suitable are esters, ethers or ketones. Typical representatives of these classes are, for example, xylene, methylnaphthalenes, liquid paraffins, cyclohexanone, ethylglycol acetate, isophorone and dibutyl phthalate. These solvents can be used alone or mixed with other components. The saturated $C_{12}$-alcohols and $C_{12}$-esters and their homologs corresponding to the compounds Ia to Id are particularly suitable formulation auxiliaries and can be regarded as synergists because they enhance the action of Ia, Ib, Ic and Id.

It is furthermore possible to prepare solutions in vegetable, animal or synthetic oils or fats and other evaporation-inhibiting solvents with a low vapor pressure such as dioctyl phthalate for the purpose of prolonging the action.

It is furthermore possible for the mixture to be bound in or on natural or synthetic solid carriers such as rubber, cork, cellulose, plastics, ground carbon, sawdust, silicates, crushed pumice, terracotta or similar solid carriers, or to be employed in special capsule formulations or plastic containers in order in this way to achieve uniform release to the air over lengthy periods. The agent can also be evaporated from suitable containers, e.g. capillaries, rubber tubes or other vessels, through narrow orifices or by diffusion through the container wall and from multilayer plastic plates, called flakes, which results in particularly uniform concentrations of the scent over lengthy periods.

The content of mixture in these compositions can vary within wide limits. In general the agent: additive ratio can be in the range from 10:1 to 1:$10^3$, for example In capsule formulations or other suitable containers, the agent can, for example, be used in pure, undiluted form and its content can be very high and up to 90% of the weight of the complete formulation. However, in general very low agent concentrations in the compositions suffice in order to exert the desired effect on male codling moths. A preferred agent: additive ratio is from 1:3 to 1:$10^2$, in particular from 1:10 to 1:100.

PREPARATION EXAMPLES

EXAMPLE 1

A mixture of 40 g of 8-chlorooctanol, 0.1 g of acetic acid and 60 g of tert-butyl methyl ether and a mixture of 17 g of ethyl vinyl ether and 83 g of tert-butyl methyl ether were added separately but simultaneously to 250 ml of tert-butyl methyl ether. After the addition was complete, the mixture was stirred at 20° C. for 12 h. To work up the mixture it was washed three times with 300 ml of saturated sodium bicarbonate solution each time, and the organic phase was dried with sodium sulfate and concentrated. The chloro acetal was obtained in a yield of 235 g (85% pure)=84%.

EXAMPLE 2

77 g of crotonaldehyde are slowly added to 260 g of 8-chlorooctyl 1-ethoxyethyl ether and 35 g of magnesium in 2 l of THF at −10° C. The mixture is left to stir at −10° C. for 1 h, hydrolyzed with 2 l of saturated ammonium chloride solution, and the organic phase is separated off. The aqueous phase is extracted several times with toluene, and the extracts are combined with the major amount and dried over sodium sulfate and concentrated. The crude product is purified by molecular distillation at 190° C. under 1 mbar.

Yield: 259 g (85% pure)=80%

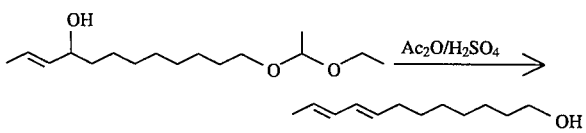

3.15 g of concentrated sulfuric acid are added to a solution of 33 g of acetic anhydride and 122 g of 9-hydroxy-10-dodecenyl 1-ethoxyethyl ether in 300 ml of dioxane at 0° C. and the mixture is stirred at 0° C. for 1.5 h. A solution composed of 225 ml of a 13.25% strength sodium chloride solution and 4 g of sodium hydroxide is then added, and the mixture is stirred at 0° to 10° C. for 20 min. The organic phase is isolated, dried and stirred with 1 g of 4-chlorothiophenol at 100° C. for 4 h. The mixture is extracted once with 25 ml of 25% strength sodium hydroxide solution, washed twice with water to neutralize and distilled under reduced pressure.

Yield: 55 g=80% (mixture of isomers, E,E isomer content: 45%)

Boiling point: 120° C./0.1 mbar.

The following halo acetals V can be prepared as described in Example 1:

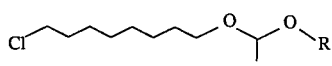

R=methyl, ethyl, propyl, isopropyl, butyl, isobutyl, pentyl, hexyl, cyclohexyl, 8-halooctyl.

The following alkenols VI can be prepared as described in Example 2:

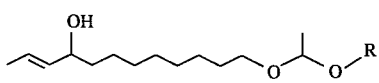

R=methyl, ethyl, propyl, isopropyl, butyl, isobutyl, pentyl, hexyl, cyclohexyl, 9-hydroxy-10-dodecenyl.

USE EXAMPLES

The efficacy of novel pheromone products at interfering with mating can at present be determined only in large-scale trials because no valid laboratory tests are available.

A mixture of isomers which was prepared as described in Example 3 and had the following composition was employed:

8E,10E-dodecadienol 45%

Total of other isomers 40%

The agent was dispensed into polyethylene ampoules. One ampoule contains about 500 mg of the product according to the invention, and the second contains about 400 mg of 11Z-tetradecenyl acetate, the pheromone of the tortrix moth *Adoxophyes orana*. The ampoules are distributed uniformly in the orchards before the pests start to fly (about 500 ampoules/ha) (Table 1).

TABLE 1

| Location | Area ha | Infestation with codling moths | Infestation with tortrix moths |
| --- | --- | --- | --- |
| Bölingen | 3.5 | + | + |
| Krefeld | 3.0 | + | + |
| Bauschlott | 6.0 | − | − |
| Dieblich | 1.0 | + | + |
| Bad Hönig | 4.5 | + | + |

At only one site was the objective not achieved.

At 8 locations for comparison the known 8E,10E-dodecadienol was applied, likewise 500 mg/ampoule and combined with the tortrix moth pheromone. At three locations during the season the economic threshold of damage of 1% infestation was exceeded (Table 2).

TABLE 2

| Location | Area ha | Infestation with codling moths | Infestation with tortrix moths |
| --- | --- | --- | --- |
| Kriftel | 2.0 | + | + |
| Mainz | 2.0 | + | + |
| Dieblich | 3.0 | + | − |
| Urmitz | 0.4 | + | + |
| Bauschlott | 6.0 | − | − |
| Geisenheim | 3.0 | − | − |
| Bölingen | 3.4 | − | − |
| Krefeld | 3.0 | + | + |

+ Infestation below threshold of damage (1%)
− Infestation above threshold of damage (1%)

It was thus shown that in large-scale trials relevant to practice the mixture of isomers is sufficiently effective. Surprisingly, the results with the known agent tended to be worse than with the mixture of isomers according to the invention.

Another advantage of the novel method is that the mixture of isomeric 8,10-dodecadienols can be used without formulation aids. Hitherto it has been necessary to employ the pure agent 8E,10E-dodecadienol together with formulation aids such as saturated $C_{12}$-esters and homologs in order to obtain constant rates of evaporation. The possibility of dispensing with formulation aids means an additional advantage.

We claim:

1. A method for controlling the codling moth *Cydia pomonella* by interfering with mating, which comprises applying a composition containing a mixture of proportions of isomers 8E,10E-dodecadienol (Ia), 8E,10Z-dodecadienol (Ib), 8Z,10E-dodecadienol (Ic), 8Z,10Z-dodecadienol (Id) in an amount sufficient to interfere with the finding of the females by the males of the species wherein the proportion of isomers (Ib), (Ic) and (Id) in said mixture is at least 40%.

2. The method of claim 1, wherein the mixture of (Ia), (Ib), (Ic) and (Id) is prepared by the method comprising: converting 1,8-octanediol (II)

$$HO-CH_2-(CH_2)_6-CH_2-OH \qquad (II)$$

in a conventional manner in a solvent in the presence of a halogenating agent into a halo derivative of the formula (III)

$$Hal\text{-}CH_2-(CH_2)_6-CH_2-OH \qquad (III)$$

where Hal is halogen, subsequently reacting (III) with a vinyl ether of the formula (IV), $$H_2C=CH-O-R \qquad (IV)$$

where R is a C-organic radical, in a conventional manner in the presence of an acid to give an acetal of the formula (V)

$$Hal\text{-}CH_2-(CH_2)_6-CH_2-O-CH(CH_3)-OR \qquad (V)$$

converting (V) in the presence of magnesium and croton aldehyde into an alkenol of the formula (VI)

$$H_3C-CH=CH-CH(OH)-(CH_2)_8-O-CH(CH_3)-OR \qquad (VI),$$

and simultaneously eliminating from (VI) in the presence of acid the protective group R and the hydroxyl group.

3. The method as defined in claim 1 wherein the proportion of isomer (Ia) in the mixture is at least 45%.

* * * * *